(12) United States Patent
Kim (10) Patent No.: US 9,149,248 B2
(45) Date of Patent: Oct. 6, 2015

(54) METHOD FOR GENERATING TRANSVERSE ELASTIC WAVES, AND METHOD AND APPARATUS FOR ACQUIRING IMAGES USING TRANSVERSE ELASTIC WAVES

(75) Inventor: Taeyong Kim, Seongnam-si (KR)

(73) Assignee: Alpinion Medical Systems Co., Ltd. (KR)

( * ) Notice: Subject to any disclaimer, the term of this patent is extended or adjusted under 35 U.S.C. 154(b) by 284 days.

(21) Appl. No.: 13/266,883

(22) PCT Filed: Apr. 27, 2010

(86) PCT No.: PCT/KR2010/002617
§ 371 (c)(1),
(2), (4) Date: Jan. 4, 2012

(87) PCT Pub. No.: WO2010/126264
PCT Pub. Date: Nov. 4, 2010

(65) Prior Publication Data
US 2012/0116225 A1 May 10, 2012

(30) Foreign Application Priority Data
Apr. 29, 2009 (KR) ........................ 10-2009-0037529

(51) Int. Cl.
*A61B 8/13* (2006.01)
*A61B 8/00* (2006.01)
*A61B 8/08* (2006.01)
*G01S 7/52* (2006.01)

(52) U.S. Cl.
CPC . *A61B 8/00* (2013.01); *A61B 8/485* (2013.01); *G01S 7/52036* (2013.01); *G01S 7/52042* (2013.01)

(58) Field of Classification Search
None
See application file for complete search history.

(56) References Cited

U.S. PATENT DOCUMENTS

| 5,810,731 A * | 9/1998 | Sarvazyan et al. | 600/438 |
| 7,252,004 B2 * | 8/2007 | Fink et al. | 600/443 |
| 8,118,744 B2 * | 2/2012 | Palmeri et al. | 600/437 |

(Continued)

FOREIGN PATENT DOCUMENTS

| EP | 0068052 B1 * | 11/1986 | ............ G01S 7/5206 |
| KR | 200270831 Y1 | 4/2002 | |

(Continued)

OTHER PUBLICATIONS

English translation of the International Search Report for PCT/KR2010/002617, mailed Dec. 27, 2010; ISA/KR.

(Continued)

*Primary Examiner* — Long V Le
*Assistant Examiner* — Kevin Pontius
(74) *Attorney, Agent, or Firm* — Harness, Dickey & Pierce, P.L.C.

(57) ABSTRACT

The present invention relates to a method for generating transverse elastic waves, a method and apparatus for acquiring images using the transverse elastic waves. The present disclosure provides a technique for generating transverse elastic waves by focusing the ultrasonic waves respectively on a number of focal points which are virtually present in a viscoelastic medium and also become wave sources of the transverse elastic waves, and controlling the generated transverse elastic waves to have peak positions with their overlapping points residing and translating in two line segments extending in parallel or at an acute angle to facilitate increasing elastic deformations of the viscoelastic medium to an appropriate level, and thus acquiring images with improved accuracy in the viscoelastic medium.

14 Claims, 8 Drawing Sheets

(56) References Cited

U.S. PATENT DOCUMENTS

| | | |
|---|---|---|
| 8,500,639 B2 * | 8/2013 | Yao .............................. 600/438 |
| 8,734,352 B2 * | 5/2014 | Burcher et al. ............... 600/442 |
| 2004/0167403 A1 | 8/2004 | Nightingale et al. |
| 2012/0123262 A1 * | 5/2012 | Xie et al. ...................... 600/438 |

FOREIGN PATENT DOCUMENTS

| | | | |
|---|---|---|---|
| KR | 1020050013604 A | 2/2005 | |
| KR | 10-0782045 B1 | 11/2007 | |
| KR | 10-0830638 B1 | 5/2008 | |
| WO | WO-2007110375 A1 | 10/2007 | |
| WO | WO 2008139245 A1 * | 11/2008 | ............... A61B 8/08 |

OTHER PUBLICATIONS

English translation of the International Preliminary Report on Patentability (Chapter I of the Patent Cooperation Treaty) for PCT/KR2010/002617, issued Nov. 9, 2011.

* cited by examiner

METHOD FOR GENERATING TRANSVERSE ELASTIC WAVES, AND METHOD AND APPARATUS FOR ACQUIRING IMAGES USING TRANSVERSE ELASTIC WAVES

TECHNICAL FIELD

The present disclosure relates to a method for generating transverse elastic waves, and to a method and apparatus for acquiring images using transverse elastic waves. More particularly, the present invention relates to a technique used for checking or diagnosing the condition of a tissue within a viscoelastic medium.

BACKGROUND ART

The statements in this section merely provide background information related to the present disclosure and may not constitute the prior art.

There are active researches and developments of methods for using ultrasound to check the internal status of materials, or applying it to diagnosis and treatment toward human health as medical field and some other industrial areas have already commercialized the applied ultrasonic technologies.

An exemplary application of ultrasound in medical field is diagnosis such as prenatal diagnosis or cancerous tissue diagnostics, and therapies such as fat removal or destruction of cancerous tissue (or malignant tumors).

A method is recently known for acquiring images of elastic deformations inside the viscoelastic medium by giving a strong impact of focused ultrasonic waves to a point of the viscoelastic medium and thus using transverse elastic waves generated from the focal point as being the wave source. One of the related techniques is suggested by Korean Patent Registration No. 10-0782045 invented by Kim; Cheol An, et al., assigned to Medison Co., Ltd., and entitled ultrasonic diagnostic system for providing elastic image with additional information.

If two substances with different moduli of elasticity are subject to transverse elastic waves generated, the substances experience different elastic deformations. For example, since such tissue of the body as cancer or tumor is more solid than normal surrounding tissue, the former deforms less than the latter by the transverse elastic waves. This enables the chronological sequence of images to be acquired and visualized corresponding to elastic deformations of tissues by propagations of the transverse elastic wave from the focusing of ultrasonic waves and thereby observing and diagnosing the internal state of the tissues.

In general, since a small impact of the focused ultrasonic waves at a point (hereinafter called 'focal point') causes a minute elastic deformation, an adequately accurate diagnosis of a tissue needs the viscoelastic medium to have greater elastic deformations by generating stronger transverse elastic waves from focusing high-intensity ultrasonic waves to more accurately diagnose the viscoelastic medium tissue.

However, when applying such use of transverse elastic waves to body tissue, the heat generated at the focus areas by the ultrasonic waves may cause destruction of the normal tissue and excessive deformations of the focus areas to give rise to an incoherence within the tissue, which undesirably puts the body under too much strain of the high-intensity focused ultrasonic signals for longer than a proper period of time (exposure time).

On the other hand, International Publication No. WO2007/110375 invented by Jérémy Bercoff, David Sabery, et al. and coapplied by Super Sonic Imagine (Titled A Method and A Device for Imaging A Visco-elastic Medium) suggests a technology to focus ultrasonic waves on a number of locations, simultaneously or in alternation.

DISCLOSURE

Technical Problem

The present disclosure is directed to providing a technique for controlling transverse elastic waves generated by focusing ultrasonic waves at multifocal points so that peak positions of the transverse elastic waves under a mutual interference have overlapping points residing in and translating in two line segments extending in parallel or at an acute angle.

Technical Solution

In a method for generating transverse elastic waves to achieve the object of the present disclosure, ultrasonic signals are focused on each of number M (M≥2) of focal points which reside on a virtual line segment within a viscoelastic medium and focused on which M focal points are the ultrasonic signals emitted respectively from different ultrasonic signal sources.

In addition, according to a specific aspect of the present disclosure, the ultrasonic signals focused on each of M focal points are at a same focal time and equidistant.

Meanwhile, according to another specific aspect of the present disclosure, the ultrasonic signals are focused on each of M focal points with a time interval, and M focal points are equally distanced in the order of numbers 1 to M. Then, the ultrasonic signals are emitted in a sequential focusing on the focal points starting from focus 1 to focus M at the equal time interval.

Further, the ultrasonic signals focused on each of M focal points have a same ultrasonic pressure.

A method for acquiring images using transverse elastic waves to achieve the objects of the present disclosure includes a step A for focusing ultrasonic signals on each of number M (M≥2) of focal points residing in a virtual line segment within a viscoelastic medium; and a step B for acquiring and then imaging a deformation signal of the viscoelastic medium due to propagations of transverse elastic waves generated from the step A of focusing the ultrasonic signals, wherein the ultrasonic signals focused on the number M of focal points in the step A are emitted respectively from different ultrasonic signal sources.

According to a specific aspect of the method for acquiring images using the transverse elastic waves of the present disclosure, the ultrasonic signals focused on each of M focal points are at a same focal time and equally distanced.

Meanwhile, according to another specific aspect of the method for acquiring images using the transverse elastic waves of the present disclosure, the ultrasonic signals are focused on each of M focal points with a time interval, and M focal points are equally distanced in the order of numbers 1 to M. Then, the ultrasonic signals are emitted in a sequential focusing on the focal points starting from focus 1 to focus M at the equal time interval.

Further, the ultrasonic signals focused on each of M focal points have a same ultrasonic pressure.

A method for acquiring images using transverse elastic waves according to yet another aspect of the present disclosure includes a step A for controlling transverse elastic waves generated by emitting a plurality of ultrasonic waves into a viscoelastic medium to propagate so that peak positions of the transverse elastic waves under a mutual interference have overlapping points residing and translating in two line segments extending in parallel; and a step B for acquiring and then imaging a deformation signal of the viscoelastic medium due to propagations of transverse elastic waves carried out in the step A of controlling the transverse elastic waves.

A method for acquiring images using transverse elastic waves according to yet another aspect of the present disclosure includes a step A for controlling transverse elastic waves generated by emitting a plurality of ultrasonic waves into a viscoelastic medium to propagate so that peak positions of the transverse elastic waves under a mutual interference have overlapping points residing and translating in two line segments extending at an acute angle; and a step B for acquiring and then imaging a deformation signal of the viscoelastic medium due to propagations of transverse elastic waves carried out in the step A of controlling the transverse elastic waves.

An apparatus for acquiring images using transverse elastic waves according to yet another aspect of the present disclosure includes an ultrasonic wave emitter for focusing ultrasonic signals on each of number M (M≥2) of focal points residing in a virtual line segment within a viscoelastic medium; a signal acquisitor for acquiring a signal of the viscoelastic medium deformed due to the transverse elastic waves generated by focusing ultrasonic signals emitted by the ultrasonic wave emitter; an imager for imaging the signal acquired by the signal acquisitor; and a controller for controlling each of the ultrasonic wave emitter, the signal acquisitor, and the imager, wherein the ultrasonic wave emitter is provided with a plurality of ultrasonic signal sources.

The plurality of ultrasonic signal sources may be provided along a line or in a form of rectangular matrix.

According to a specific aspect of the apparatus for acquiring images using transverse elastic waves of the present disclosure, the controller controls the plurality of ultrasonic signal sources to focus the ultrasonic signals emitted from the plurality of ultrasonic signal sources on the number M of focal points at the same time.

Meanwhile, according to a specific aspect of the apparatus for acquiring images using transverse elastic waves of the present disclosure, the controller controls the plurality of ultrasonic signal sources to focus the ultrasonic signals emitted from the plurality of ultrasonic signal sources onto each of the number M of focal points at a time interval. In addition, the number M of focal points are equally distanced in numerical order of focal point Nos. 1 to M, and the controller controls the plurality of ultrasonic signal sources to focus the ultrasonic signals on the focal points sequentially from focal point No. 1 to focal point No. M at an equal time interval.

Advantageous Effects

As mentioned above, according to the present disclosure, since the transverse elastic waves are generated by focusing ultrasonic waves on a number of focal points simultaneously or sequentially and the generated transverse elastic waves are controlled to have peak positions under a mutual interference with overlapping points residing in and translating in two line segments extending in parallel or at an acute angle, it has become easy to increase the elastic deformations of the viscoelastic medium to an appropriate level (up to 720 mW/cm2) for enhanced sharpness of the elastic deformation images while keeping the focused ultrasonic wave power density low with the increased elastic deformations of the viscoelastic medium, and in particular, guiding the peak positions to reside on and translating in the two line segments at the acute angle allows observations of the elastic deformations of the viscoelastic medium at diverse angles and thereby provides accurate exams and diagnoses inside of the viscoelastic medium.

MODE FOR INVENTION

Hereinafter, preferred aspects of the present disclosure will be described in more detail with reference to the accompanying drawings, although well known or repeated descriptions will be omitted for the sake of conciseness.

Imager Using Transverse Elastic Wave for Example

Figure 1:
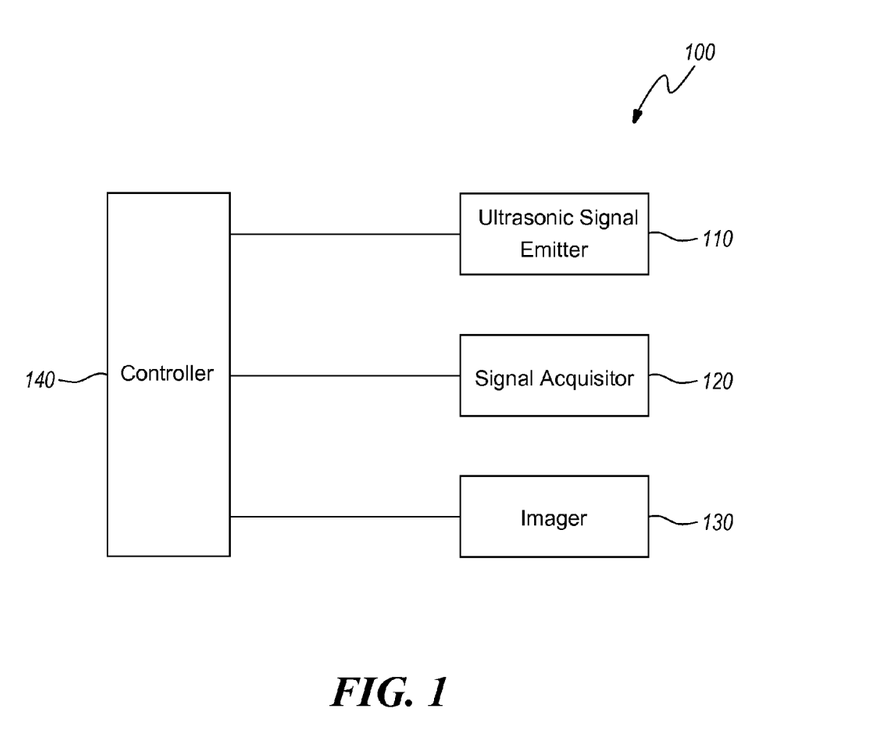
FIG. 1 is a diagram illustrating a configuration of an apparatus for acquiring images using transverse elastic waves according to an aspect.

FIG. 1 is a diagram illustrating a configuration of an apparatus 100 for acquiring images using transverse elastic waves (hereinafter called 'image acquisition apparatus') according to an aspect.

As shown in FIG. 1, image acquisition apparatus 100 of the aspect comprises an ultrasonic signal emitter 110, a signal acquisitor 120, an image generator or imager 130, a controller 140, and the like.

Figure 2:
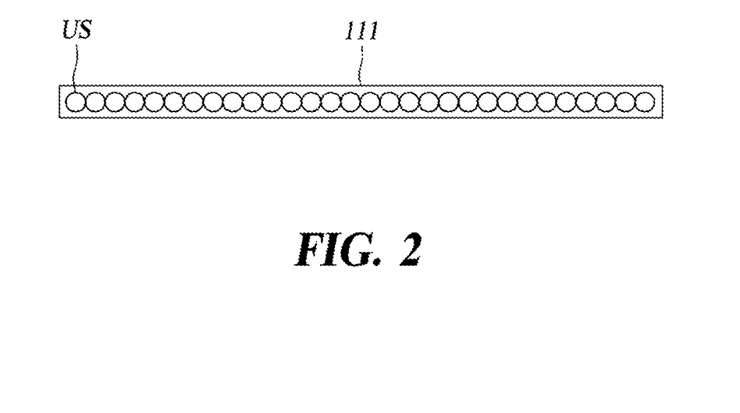
FIG. 2 is a diagram illustrating an ultrasonic wave emitter applied to the apparatus for acquiring images using transverse elastic waves of FIG. 1.
Figure 3:
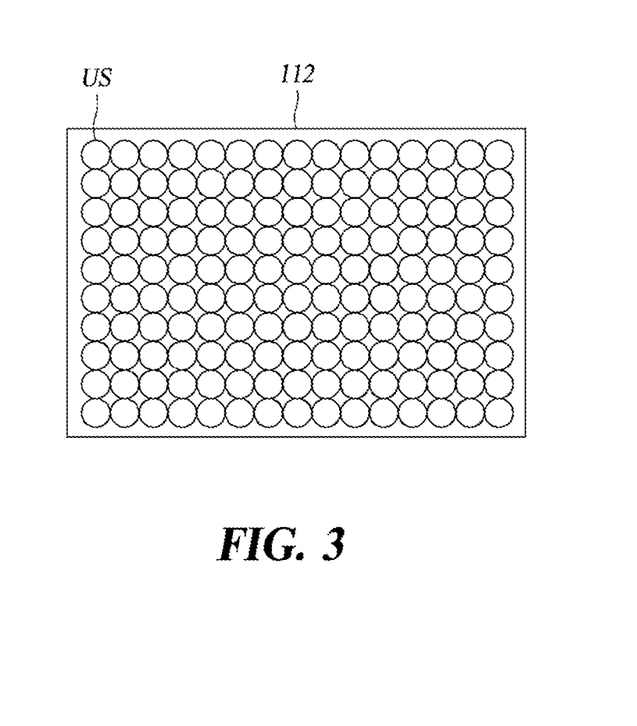
FIG. 3 is a diagram illustrating an alternative ultrasonic wave emitter applied to the apparatus for acquiring images using transverse elastic waves of FIG. 1.

Ultrasonic signal emitter 110 is adapted to focus ultrasonic signals on each of a number of focal points residing in a virtual line segment within a viscoelastic medium, and it may be in the configurations illustrated in FIG. 2 or 3.

Ultrasonic signal emitter 110 in FIG. 2 has a plurality of ultrasonic signal sources (US) along a line, and ultrasonic signal emitter 110 according to FIG. 3 is provided with a plurality of ultrasonic signal sources (US) in a form of matrix.

Signal acquisitor 120 acquires a signal of the viscoelastic medium deformed due to the transverse elastic waves generated by focusing ultrasonic signals emitted by the ultrasonic wave emitter 110. Signal acquisitor 120 may be provided as a separate unit from ultrasonic signal emitter 110 or as a single unit with ultrasonic wave emitter 110 as in Korean Patent Registration No. 10-830638.

As is known, imager 130 processes the signal acquired by the signal acquisitor 120 into an image.

Controller 140 controls each of the ultrasonic wave emitter 110, signal acquisitor 120, and imager 130.

Then, image acquisition apparatus 100 in this configuration enables sequentially acquired images to be displayed on monitors for visual comprehension.

Reference Remarks

Figure 4:
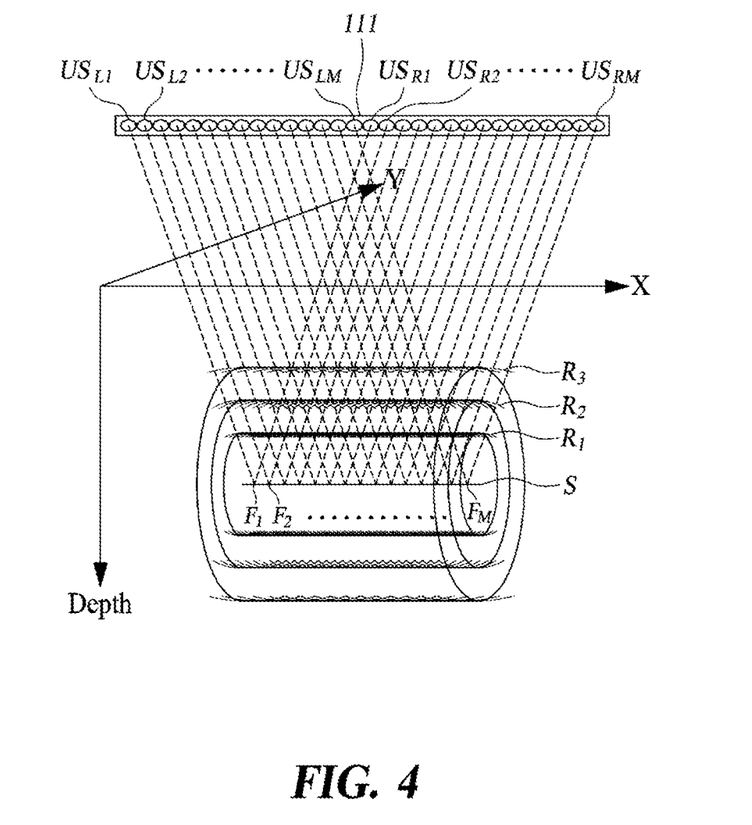
FIG. 4 is a reference diagram for describing the aspects of the present disclosure.

It is generally known that the transverse elastic wave generated by focusing an ultrasonic signal propagates in a spherical shape from the wave source of the focal point but the high energy density peak position of the transverse elastic wave translates in a diametrical bifurcation as time (T) passes on a plane perpendicular to the axial direction of a transducer of propagating the ultrasonic signal, as illustrated in FIG. 4 for reference.

Based on this information, further description will be provided on the operation of the image acquisition apparatus 100 in association with a method for generating transverse elastic waves and a method for acquiring images using the transverse elastic waves.

Method of Generating Transverse Elastic Waves for Example

Generation of the transverse elastic waves is achieved when ultrasonic wave emitter 110 emits and focuses the ultrasonic waves.

Ultrasonic wave emitter 110 focuses ultrasonic signals on each of a number of focal points residing in a virtual line segment within a viscoelastic medium and on the respective focal points of which are focused the ultrasonic signals emitted from different ultrasonic signal sources (US). This will be separately described by an aspect with an ultrasonic signal emitter 111 in FIG. 2 and another aspect with an ultrasonic signal emitter 112 in FIG. 3.

Figure 5:
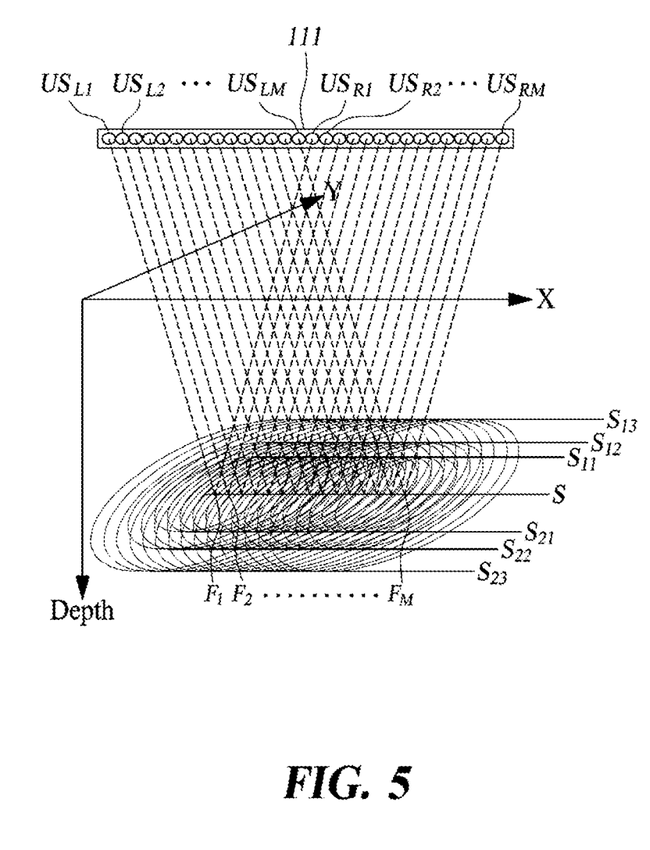
FIGS. 5 to 9 are reference diagrams for describing a method for generating the transverse elastic waves, method and operation for acquiring images using the transverse elastic waves according to the present disclosure.

Ultrasonic signal emitter 111 in FIG. 2 is equipped with a series of ultrasonic signal sources of USL1 to USLM and ultrasonic signal sources of USR1 to USRM in a line. As depicted in FIG. 5, ultrasonic signal sources of USL1 to USLM join respectively with ultrasonic signal sources of USR1 to USRM into respective pairs [(USL1, USR1), (USL2, USR2), ..., (USLM, USRM)] which focus the ultrasonic signals sequentially from a first focal point F1 to an Mth focal point FM residing in a virtual line segment S within the viscoelastic medium.

Figure 6:
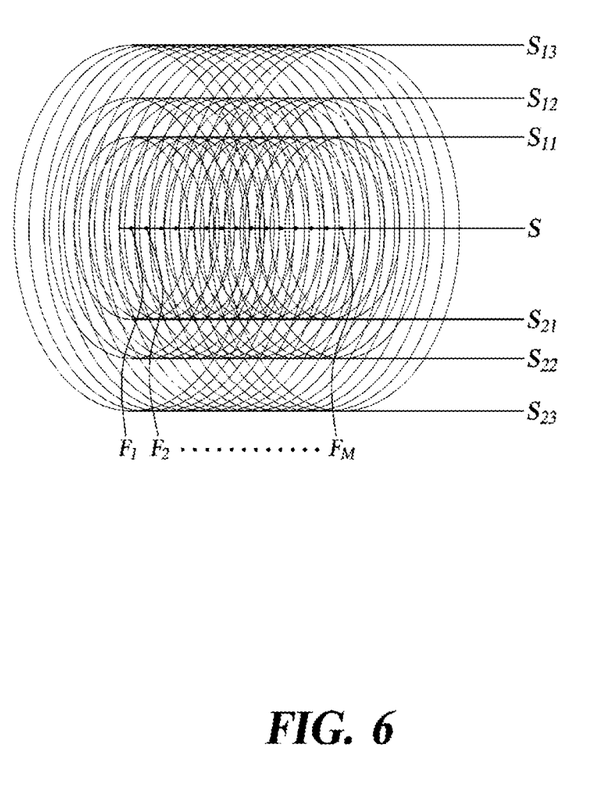

When the respective ultrasonic source pairs [(USL1, USR1), (USL2, USR2), ..., (USLM, USRM)] focus the ultrasonic signals on the respective focal points F1, F2, ..., FM simultaneously, the peak positions of the transverse elastic waves with the focal points F1, F2, ..., FM respectively used as the wave sources propagate through the viscoelastic medium as the peak positions have overlapping points residing and translating in two parallel line segments (S11/S21, S12/S22, S13/S23) extending symmetrically about a line segment (S) occupied by the focal points F1, F2, ..., FM farther away from the line segment (S), as shown in FIG. 5. FIG. 6 is a plan view in the eyes of ultrasonic signal emitter 111 with respect to the peak positions of the transverse elastic waves at the overlapping points in propagation.

Figure 7:
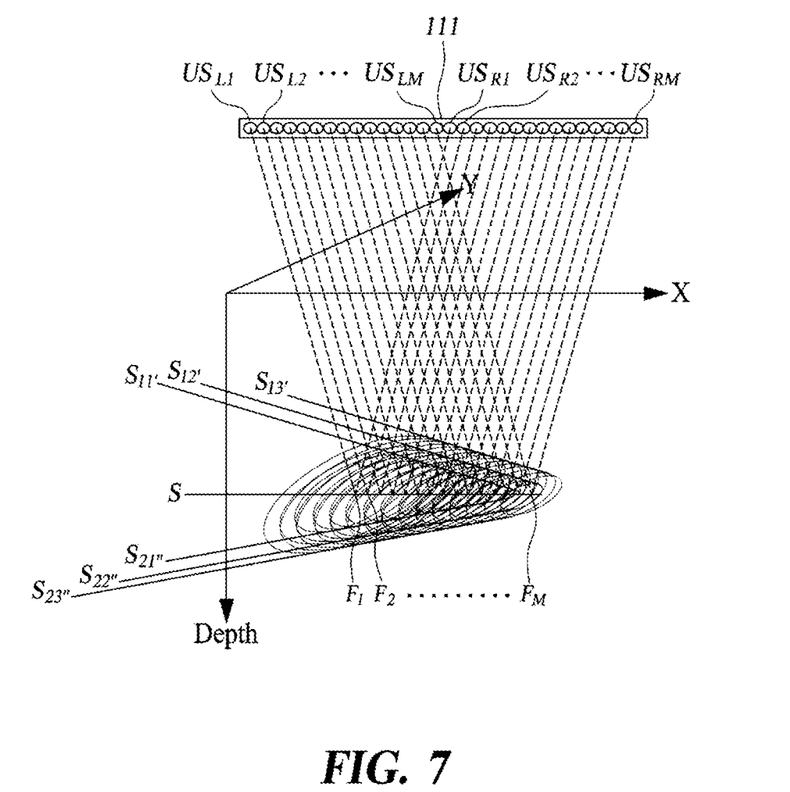
Figure 8:
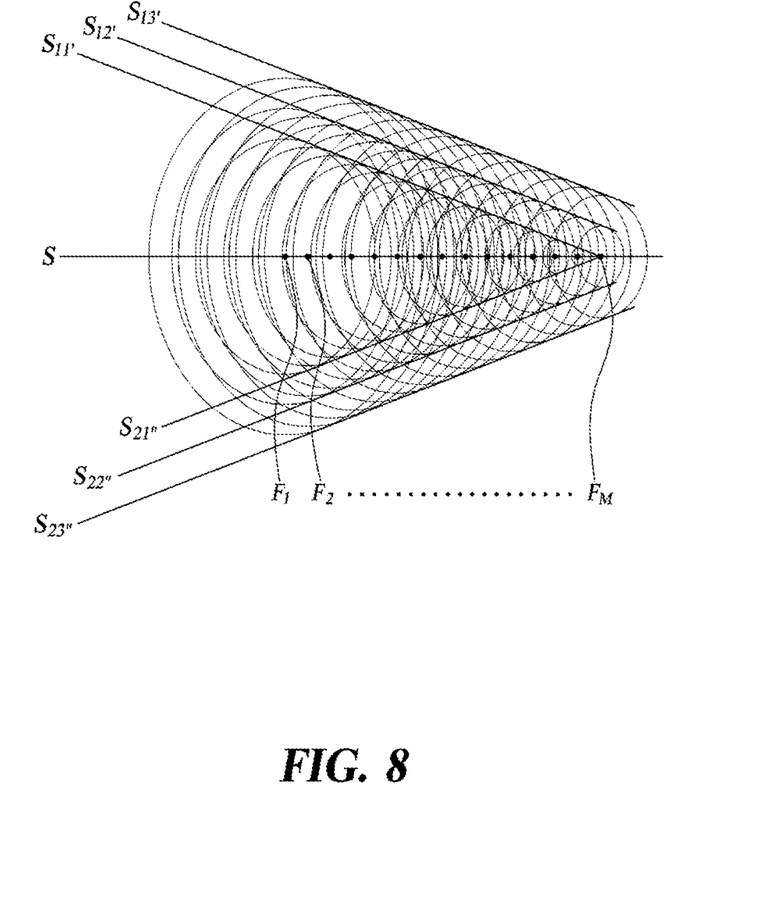

Alternatively, in the case where the respective ultrasonic source pairs [(USL1, USR1), (USL2, USR2), ..., (USLM, USRM)] focus the ultrasonic signals asynchronously, i.e. sequentially on the first focal point F1 to Mth focal point FM, then as shown in FIG. 7, the peak positions of the transverse elastic waves have overlapping points (Ra, Rb, Rc) residing and translating in two acute-angled (angled above 0 degree and below 90 degrees) line segments (S11'/S21', S12'/S22', S13'/S23') farther away from a middle line segment (S). FIG. 8 is a plan view in the eyes of ultrasonic signal emitter 111 with respect to the peak positions of the transverse elastic waves at the overlapping points in propagation.

Meanwhile, ultrasonic signal emitter 112 in FIG. 3 has a matrix form of ultrasonic signal sources of US11 to US1N, ultrasonic signal sources of US21 to US2N, and ultrasonic signal sources of USM1 to USMN.

Figure 9:
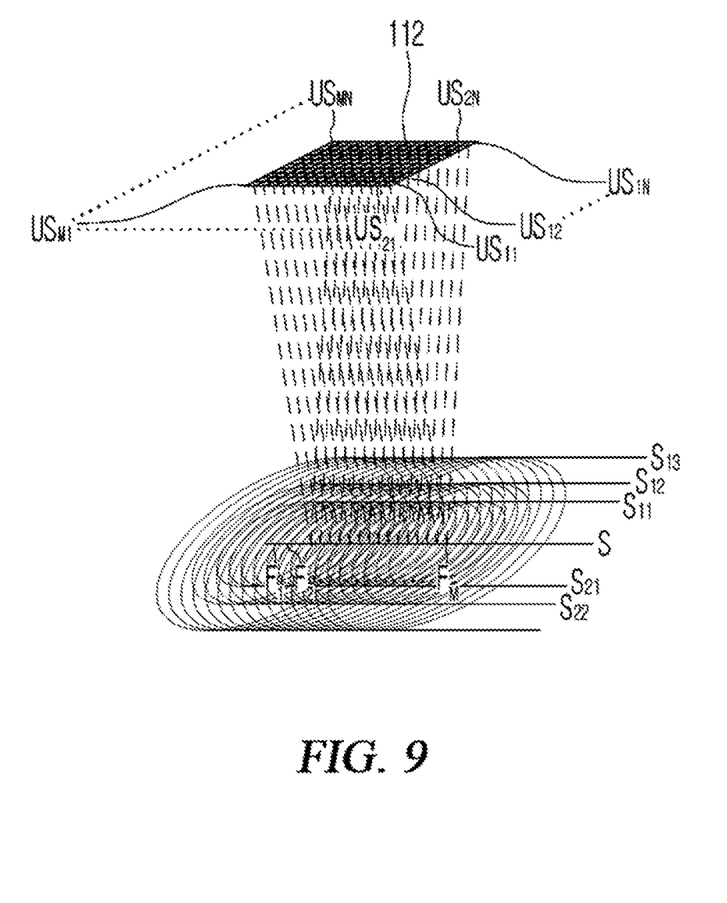

As shown in FIG. 9, ultrasonic signal sources of US11 to US1N are present in ultrasonic source pairs for focusing the ultrasonic signals on a first focal point F1. Ultrasonic signal sources of US21 to US2N are in turn provided to focus the ultrasonic signals on a second focal point F2, and ultrasonic signal sources of USM1 to USMN focus the ultrasonic signals on an Mth focal point FM.

Therefore, when the respective ultrasonic source pairs [(US11 to US1N), (US21 to US2N) ..., (USM1 to USMN)] focus the ultrasonic signals on the respective focal points (F1 F2, ..., FM) simultaneously as shown in FIG. 9, the peak positions of the generated transverse elastic waves have overlapping points residing and translating in two parallel line segments; and in the case where the same respective ultrasonic source pairs [(US11 to US1N), (US21 to US2N) ..., (USM1 to USMN)] focus the ultrasonic signals with time intervals and sequentially on the respective focal points (F1 F2, ..., FM), the peak positions of the generated transverse elastic waves have overlapping points residing and translating in two acute-angled line segments.

Here, to reinforce the elastic deformations of the viscoelastic medium to an appropriate level while keeping the overlapping points of the peak positions of the transverse elastic waves to more accurately parallel or acute-angled line segments, there is a need to have more than three focal points which are equidistant, and it is preferable that the ultrasonic signals focused on the respective focal points have a common ultrasonic pressure. Especially, to more accurately register the overlapping points of the transverse elastic wave peak positions to the more exactly acute-angled line segments, it is preferable to focus an arrangement of ultrasonic waves in a numerical order from No. 1 to M focus at an equal time interval.

Method for Acquiring Images Using Transverse Elastic Waves for Example

When the described method generates the transverse elastic waves by focusing the ultrasonic signals simultaneously or sequentially on the plurality of focal points F1 F2, ..., FM, the transverse elastic waves generated propagate so that the transverse elastic wave peak positions have overlapping points residing in and translating in two parallel or acute-angled line segments and thereby exerting an appropriately strong pressure to the overlapping points of the peak positions which then undergo elastic deformations.

Then, signal acquisitor 120 acquires deformation signals of the viscoelastic medium under the elastic deformations, and imager 130 acquires images by imaging the deformation signals from signal acquisitor 120.

Of course, the images acquired sequentially in time will be expressed visually through a monitor or other displaying means.

Although detailed descriptions have been made by the aspects of the present disclosure referring to the drawings attached, presented above are preferable examples only and the present disclosure should not be understood restrictedly by the very aspects stated but the scope of right of the present disclosure should be understood as being what is claimed below and its equivalent idea.

CROSS-REFERENCE TO RELATED APPLICATION

If applicable, this application claims priority under 35 U.S.C §119(a) on Patent Application No. 10-2009-0037529 filed in Korea on Apr. 29, 2009, the entire content of which is hereby incorporated by reference. In addition, this non-provisional application claims priority in countries, other than the U.S., with the same reason based on the Korean Patent Application, the entire content of which is hereby incorporated by reference.

The invention claimed is:

1. A method comprising:
   generating transverse elastic waves from ultrasonic signals focused on each of number M (M≥3) of focal points residing in a virtual line segment within a viscoelastic medium, wherein focused on the number M of focal points are the ultrasonic signals emitted respectively from different ultrasonic signal sources; and
   spacing apart the number M of focal points equidistant to one another so that lines connecting peak points generated by superposition of the transverse elastic waves propagate in two opposite directions at an acute angle when the focal points are excited at an equal time interval.

2. The method for generating transverse elastic waves of claim 1, wherein the ultrasonic signals focused on each of the number M of focal points are at a same focal time.

3. The method for generating transverse elastic waves of claim 1, wherein the ultrasonic signals focused on each of the number M of focal points have a same ultrasonic pressure.

4. The method for generating transverse elastic waves of claim 1, wherein the number M of focal points are arranged in numerical order of focal point Nos. 1 to M, and the ultrasonic signals are emitted to be focused on the focal point Nos. 1 to M sequentially.

5. A method for acquiring images using transverse elastic waves comprising:
   focusing ultrasonic signals on each of number M (M≥3) of focal points residing in a virtual line segment within a viscoelastic medium;
   acquiring and then imaging a deformation signal of the viscoelastic medium due to propagations of transverse elastic waves generated from the step of focusing the ultrasonic signals, wherein the ultrasonic signals focused on the number M of focal points in the step of focusing are emitted respectively from different ultrasonic signal sources; and
   spacing apart the number M of focal points equidistant to one another so that lines connecting peak points generated by superposition of the transverse elastic waves propagate in two opposite directions at an acute angle when the focal points are excited at an equal time interval.

6. The method for acquiring images using transverse elastic waves of claim 5, wherein the ultrasonic signals focused on each of the number M of focal points are at a same focal time.

7. The method for acquiring images using transverse elastic waves of claim 5, wherein the ultrasonic signals focused on each of the number M of focal points have a same ultrasonic pressure.

8. The method for acquiring images using transverse elastic waves of claim 5, wherein the number M of focal points are arranged in numerical order of focal point Nos. 1 to M, and the ultrasonic signals are emitted to arrive at the focal point Nos. 1 to M sequentially.

9. A method for acquiring images using transverse elastic waves comprising:
   controlling transverse elastic waves generated by emitting ultrasonic waves on each of number M (M≥3) of focal points residing in a virtual line segment within a viscoelastic medium to propagate, wherein the number M of focal points are spaced apart equidistant to one another and receive the ultrasonic waves with an equal time interval therebetween so that lines connecting peak points generated by superposition of the transverse elastic waves propagate in two opposite directions at an acute angle when the focal points are excited at an equal time interval; and
   acquiring and then imaging a deformation signal of the viscoelastic medium due to propagations of transverse elastic waves carried out in the step of controlling the transverse elastic waves.

10. An apparatus for acquiring images using transverse elastic waves comprising:
    an ultrasonic wave emitter for focusing ultrasonic signals on each of number M (M≥3) of focal points residing in a virtual line segment within a viscoelastic medium;
    a signal acquisitor for acquiring a signal of the viscoelastic medium deformed due to the transverse elastic waves generated by focusing ultrasonic signals emitted by the ultrasonic wave emitter;
    an imager for imaging the signal acquired by the signal acquisitor;
    a controller for controlling each of the ultrasonic wave emitter, the signal acquisitor, and the imager, wherein the ultrasonic wave emitter is provided with a plurality of ultrasonic signal sources; and
    spacing apart the number M of focal points equidistant to one another so that lines connecting peak points generated by superposition of the transverse elastic waves propagate in two opposite directions at an acute angle when the focal points are excited at an equal time interval.

11. The apparatus for acquiring images using transverse elastic waves of claim 10, wherein the plurality of ultrasonic signal sources are provided along a line or in a form of rectangular matrix.

12. The apparatus for acquiring images using transverse elastic waves of claim 10, wherein the plurality of ultrasonic signal sources are provided in a form of matrix.

13. The apparatus for acquiring images using transverse elastic waves of claim 11 or 12, wherein the controller controls the plurality of ultrasonic signal sources to focus the ultrasonic signals emitted from the plurality of ultrasonic signal sources on the number M of focal points at the same time.

14. The apparatus for acquiring images using transverse elastic waves of claim 12, wherein the number M of focal points are arranged in numerical order of the focal point Nos. 1 to M, and the controller controls the plurality of ultrasonic signal sources to focus the ultrasonic signals on the focal points sequentially from focal point No. 1 to focal point No. M.

* * * * *